United States Patent [19]

Louks et al.

[11] Patent Number: 4,547,597

[45] Date of Patent: Oct. 15, 1985

[54] PREPARATION OF HALOGENATED PHENOLS

[75] Inventors: David H. Louks, Saginaw; Leonard R. Thompson; Wayne C. Muench, both of Midland, all of Mich.

[73] Assignee: The Dow Chemical Company, Midland, Mich.

[21] Appl. No.: 495,382

[22] Filed: May 17, 1983

[51] Int. Cl.[4] .............................................. C07C 39/24
[52] U.S. Cl. .................................... 568/779; 568/774
[58] Field of Search .................................. 568/779, 774

[56] References Cited

U.S. PATENT DOCUMENTS

| | | | |
|---|---|---|---|
| 2,131,259 | 9/1938 | Stoesser | 568/776 |
| 2,440,602 | 4/1948 | Foster | 568/779 |
| 2,494,993 | 1/1950 | Foster | 568/779 |
| 2,662,918 | 12/1953 | Spaulding | 568/779 |
| 3,038,882 | 6/1962 | Galvin et al. | 568/726 |
| 3,542,882 | 11/1970 | Ashall | 568/779 |
| 3,965,158 | 6/1976 | Sorela | 568/779 |
| 4,376,220 | 3/1983 | Waltzel | 568/779 |
| 4,431,847 | 2/1984 | Bossier | 568/779 |

FOREIGN PATENT DOCUMENTS

| | | | |
|---|---|---|---|
| 2632565 | 2/1976 | Fed. Rep. of Germany | 568/779 |
| 2726436 | 12/1977 | Fed. Rep. of Germany | 568/779 |
| 6512570 | 4/1965 | Netherlands | 568/779 |
| 1460214 | 12/1976 | United Kingdom | 568/774 |

OTHER PUBLICATIONS

R. S. Drago et al., J.A.C.S., 84, 2696–2699 (1962).
M. D. Joesten et al., J.A.C.S., 84, 3817–3821 (1962).

Primary Examiner—Werren B. Lone

[57] ABSTRACT

Halogenated phenolic compounds are prepared by forming a low melting point complex of the phenolic compound and contacting the low melting point complex with a halogenating agent under halogenating conditions.

14 Claims, No Drawings

PREPARATION OF HALOGENATED PHENOLS

BACKGROUND OF THE INVENION

The present invention relates to the preparation of halogenated phenolic compounds. More particularly the present invention relates to an improved process for the direct halogenation of phenolic compounds whereby reduced amounts of by-products, particularly halogenated dioxin compounds are also prepared.

Halogenated phenols such as chlorinated phenols, especially tetrachlorophenols and pentachlorophenol, are valuable fungicides that are conveniently prepared by the direct halogenation of phenol or halogenated phenols in the presence of various catalysts such as $AlCl_3$, $FeCl_3$, activated carbon and quinoline, tellurium and various salts thereof, as well as such catalysts in combination with various promoters such as those taught in U.S. Pat. No. 4,376,220. The preferred catalyst is aluminum trichloride.

In the case of chlorinated phenols, the reaction is conducted neat at a starting temperature of about 65° C.–130° C. After three or four chlorine atoms have been substituted onto the phenol, the temperature of the reaction mixture is increased to maintain a temperature approximately 10° C. above the melting point of the chlorinated mixture. The reaction is normally complete in 5–15 hours. Because the mixture's melting point increases during the later stages of the chlorination, the preparation of pentachlorophenol may require reaction temperatures of up to about 190° C. or even higher so that the reaction mixture remains in a liquid state. It is now known that elevated temperatures necessary for the preparation of highly chlorinated phenols are particularly conducive to the formation of increased amounts of undesirable by-products particularly chlorinated dibenzo-p-dioxins.

In U.S. Pat. No. 2,131,259, it is further taught to employ solvents such as chlorinated aliphatic compounds in the reaction, thereby allowing the use of lower reaction temperatures while maintaining a liquid reaction mixture. Suitable solvents included ethylene dichloride, sym-tetrachloroethane, trichloroethane, carbon tetrachloride and propylene chloride. The use of such solvents has not proven to be practical in commercial usage due to the possible formation of solvent-reactant by-products as well as the increased production costs associated with removal and recycle of solvent during the process, and decreased effectiveness of the chlorination process due to the solvent's dilution effect.

It would be desirable to provide a process that is capable of preparing highly halogenated phenolic derivatives without concomitant formation of substantial amounts of by-products. It would further be desirable to provide a process that would-allow the preparation of highly halogenated phenolic compounds at reduced temperatures without the use of a solvent.

SUMMARY OF THE INVENTION

According to the present invention there is provided an improved process for halogenating phenolic compounds comprising:
 (1) forming a low melting point complex of the phenolic compound; and
 (2) contacting the low melting point complex of the phenolic compound with a halogenating agent under halogenation conditions.

DETAILED DESCRIPTION OF THE INVENTION

The phenolic compounds suitably halogenated by the present process include any aromatic compound containing phenol functionality that is capable of halogenation and which suitably forms a complex with the complex forming agents employed herein. Preferred are those phenolic compounds meeting the above criteria that are directly halogenated neat only at elevated temperatures. Most preferred are phenol itself as well as partially halogenated derivatives thereof. Especially preferred are phenol and all mono-, di-, tri- or tetrachlorinated phenols or mixtures thereof.

The halogenating agents suitably employed in the present invention include a halogen compound or a source thereof corresponding to the desired halogen functionality of the resulting product. A preferred halogenating agent is chlorine.

The conditions appropriately selected for the halogenation reaction are those previously known in the art. Generally, a catalytic amount of a Lewis acid catalyst such as aluminum trichloride or ferric chloride is employed to aid in the reaction. The catalyst is employed in an anhydrous state. Elevated temperatures of from about 50° C. to about 150° C. are employed. Preferred temperatures are those at which formation of appreciable amounts of undesirable halogenated dibenzo-p-dioxins is avoided. Preferred temperatures are from about 80° C. to about 130° C. Most preferred temperatures are from about 90° C. to about 115° C. At such temperatures, the formation of halogenated dibenzo-p-dioxin compounds is preferably less than about 50 ppm by weight and most preferably less than about 10 ppm based on the weight of the halogenated phenol product. The temperature selected will be determined by the melting point of the reaction mixture keeping in mind that the mixture is desirably maintained in the molten state. Elevated or reduced pressures may be employed as is desired. Preferred pressures are atmospheric or higher.

The formation of low melting point complexes with the phenolic reactants of the present process is accomplished using any suitable complexing agent. Included are all compounds that are capable of forming stable, isolatable complexes having a melting point less than about 150° C., preferably less than about 130° C. and most preferably less than about 115° C. Identification of suitable complexing agents may be readily determined by the skilled artisan by the simple expedient of combining the phenolic compound and the complexing agent optionally in the presence of a solvent and noting the formation of a stable complex upon isolation thereof. By the term stable is meant that the complex is sufficiently durable so as to exist independently of solvents.

Preferred complexing agents according to the present invention are the lower alkyl amide derivatives of lower aliphatic aldehydes, e.g., dimethylformamide, diethylformamide, dimethylacetamide, etc. A particularly preferred complexing agent is dimethylformamide (DMF). The melting point of the 1:1 complex of DMF and pentachlorophenol has been found to be about 62° C., allowing the neat, direct chlorination of a complex of phenol and DMF to be readily accomplished at temperatures well below 150° C., or even below 130° C. or 115° C.

The complex preferably comprises about a stoichiometric amount of the complexing agent chemically bound to the phenolic compound so as to form a stable isolatable species. Preferably, from about 0.5 to about 1.1 equivalents of the complexing agent are employed per equivalent of the phenolic compound.

After halogenation of the stable complex of the phenolic compound is completed, the product is easily recovered by simply cooling the mixture. The complex may also be recovered by dissolving in organic solvents or by any other suitable method. It has been found that the 1:1 complex of DMF and pentachlorophenol is generally more soluble in commonly employed organic solvents such as methylene chloride than is pentachlorophenol itself.

The complex may be employed in applications where previously the halogenated phenol alone has been employed. For example, it has been found that equivalent or even improved fungicidal activity on a weight basis may be obtained by use of a complex of pentachlorophenol and DMF as compared to the use of pentachlorophenol alone.

Alternatively, the complex can be easily broken and the complexing agent and halogenated phenol recovered according to well-known chemical techniques. For example, the 1:1 complex of DMF and pentachlorophenol is readily separated by dissolving the same in aqueous base and then neutralizing the base by addition of acid. Alternatively, satisfactory recovery rates may also be obtained by simply contacting the resulting complex with water.

Use of complexes of phenolic compounds according to the present invention is to be contrasted with the use of a solvent according to prior art processes in that no stable isolatable species formed by interaction of the phenol and a solvent results when a solvent is employed.

Having described the invention, the following example is provided as further illustrative and is not to be construed as limiting inasmuch as modifications thereto without departing from the scope of the invention will be readily apparent to the skilled artisan.

EXAMPLE 1

To a 3-necked, round-bottomed flask with thermowell equipped with a mechanical stirrer, a water condenser having an HCl gas scrubber attached thereto, and a chlorine addition dip tube is added 150.0 g (0.920 mole) of a mixture of 99 percent 2,4-dichlorophenol and 1 percent 2,6-dichlorophenol. After melting the dichlorophenol at 45° C. using infrared heat lamps, 0.75 g AlCl$_3$ (anhydrous) and 67.3 g (0.921 mole) DMF are added and mixed. After heating with agitation to 78° C., the chlorine gas addition is started. The reaction exotherm plus additional heating raises the temperature to 100° C. within 10 minutes, where the temperature is controlled for the remainder of the reaction. Chlorine is added at a rate of approximately 45 g/hr for 6.2 hours. Upon termination of the chlorine addition (after cooling to room temperature), there is recovered 365.4 g of yellow solid. The strong odor of HCl gas vented after storage of the product sample bottle suggests that considerable HCl and/or Cl$_2$ gas is absorbed in the reaction product.

The product is analyzed by use of gas phase chromatography employing an internal standard. The phenolic compounds are derivatized with bis(trimethylsilyl)acetamide before injection. Separation is accomplished by a 20-foot, 10 percent UCW 98 column. Determination of dimethylformamide is obtained by a 10-foot column of bonded DEGS on 80/100 Chromasorb W. AW. using an external standard.

Analysis indicated that the crude product contains about 66 weight percent pentachlorophenol, 98 percent of theoretical yield. By-product content is as follows:

| hexachlorodibenzo-p-dioxin | <0.6 ppm |
| octachlorodibenzo-p-dioxin | <1.2 ppm |
| 2,3,7,8-tetrachlorodibenzo-p-dioxin | <0.1 ppm |

It is seen that very low levels of by-product halogenated dibenzo-p-dioxins are prepared according to the presently invented process.

We claim:
1. A process for halogenating phenolic compounds comprising:
   (1) forming a low melting point complex of the phenolic compounds; and
   (2) contacting the low melting point complex of the phenolic compound in the molten state with a halogenating agent under halogenating conditions such that the halogenated phenolic compound is produced.
2. A process according to claim 1 wherein the phenolic compound is phenol, a partially halogenated derivative of phenol, or a mixture thereof.
3. The process according to claim 2 wherein the phenolic compound is phenol, a partially chlorinated derivative of phenol, or a mixture thereof.
4. A process according to claim 1 wherein the halogenating agent is chlorine.
5. A process according to claim 1 wherein a catalytic amount of a halogenation catalyst is additionally present.
6. A process according to claim 5 wherein the catalyst is aluminum trichloride or ferric chloride.
7. A process according to claim 1 wherein the reaction temperature is from about 50° C. to about 150° C.
8. A process according to claim 7 wherein the reaction temperature is from about 80° C. to about 130° C.
9. A process according to claim 8 wherein the reaction temperature is from about 90° C. to about 115° C.
10. A process according to claim 1 wherein the complex melts at a temperature less than about 150° C.
11. A process according to claim 10 wherein the complex melts at a temperature less than about 130° C.
12. A process according to claim 11 wherein the complex melts at a temperature less than about 115° C.
13. A process according to claim 1 wherein the complex comprises the reaction product of the phenolic compound with about a stoichiometric amount of a dilower alkylamide derivative of a lower alkyl aldehyde.
14. A process according to claim 1 wherein the complex comprises the reaction product of the phenolic compound with dimethylformamide, diethylformamide or dimethylacetamide.

* * * * *